US00PP32636P3

(12) United States Plant Patent
Kuiper

(10) Patent No.: US PP32,636 P3
(45) Date of Patent: Dec. 15, 2020

(54) ***ALSTROEMERIA* PLANT NAMED 'TESSUMRED'**

(50) Latin Name: *Alstroemeria hybrida*
Varietal Denomination: Tessumred

(71) Applicant: Mark Kuiper, Zandvoort (NL)

(72) Inventor: Mark Kuiper, Zandvoort (NL)

(73) Assignee: HORTIPARTNERS vof, Heerhugowaard (NL)

( * ) Notice: Subject to any disclaimer, the term of this patent is extended or adjusted under 35 U.S.C. 154(b) by 0 days.

(21) Appl. No.: 16/873,266

(22) Filed: Mar. 6, 2020

(65) Prior Publication Data

US 2020/0288616 P1 Sep. 10, 2020

Related U.S. Application Data

(60) Provisional application No. 62/919,386, filed on Mar. 9, 2019.

(51) Int. Cl.
*A01H 5/02* (2018.01)
*A01H 6/04* (2018.01)
*A01H 6/56* (2018.01)

(52) U.S. Cl.
USPC ..... Plt./309
CPC ..... *A01H 6/564* (2018.05)

(58) Field of Classification Search
USPC ..... Plt./309
See application file for complete search history.

*Primary Examiner* — Susan McCormick Ewoldt
(74) *Attorney, Agent, or Firm* — C. A. Whealy

(57) ABSTRACT

A new and distinct cultivar of *Alstroemeria* plant named 'Tessumred', characterized by its broadly upright plant habit; vigorous growth habit; freely branching habit, dense and bushy appearance; strong stems; freely flowering habit; red-colored flowers with pale yellow-colored centers; and good garden performance.

1 Drawing Sheet

Botanical designation: *Alstroemeria hybrida.*
Cultivar denomination: 'TESSUMRED'.

BACKGROUND OF THE INVENTION

The present invention relates to a new and distinct cultivar of *Alstroemeria* plant, botanically known as *Alstroemeria hybrida*, typically grown as a potted and garden plant and hereinafter referred to by the name 'Tessumred'.

The new *Alstroemeria* plant is a product of a planned breeding program conducted by the Inventor in Heerhugowaard, The Netherlands. The objective of the breeding program is to create new *Alstroemeria* plants with numerous attractive flowers and good garden performance.

The new *Alstroemeria* plant originated from a cross-pollination in September, 2010 of a proprietary selection of *Alstroemeria hybrida* identified as code designation Zh4745a, not patented, as the female, or seed, parent with a proprietary selection of *Alstroemeria hybrida* identified as code designation E1001, not patented, as the male, or pollen, parent. The new *Alstroemeria* plant was discovered and selected as a single flowering plant from within the progeny of the stated cross-pollination in a controlled greenhouse environment in Heerhugowaard, The Netherlands in August, 2012.

Asexual reproduction of the new *Alstroemeria* plant by vegetative terminal cuttings since August, 2012 has shown that the unique features of this new *Alstroemeria* plant are stable and reproduced true to type in successive generations of asexual reproduction.

SUMMARY OF THE INVENTION

The following traits have been repeatedly observed and are determined to be the unique characteristics of 'Tessumred'. These characteristics in combination distinguish 'Tessumred' as a new and distinct *Alstroemeria* plant:

1. Broadly upright plant habit.
2. Vigorous growth habit.
3. Freely branching habit, dense and bushy appearance.
4. Strong stems.
5. Freely flowering habit.
6. Red-colored flowers with pale yellow-colored centers.
7. Good garden performance.

Plants of the new *Alstroemeria* can be compared to plants of the female parent selection. Plants of the new *Alstroemeria* differ from plants of the female parent selection in the following characteristics:

1. Plants of the new *Alstroemeria* are more compact than plants of the female parent selection.
2. Plants of the new *Alstroemeria* have larger flowers than plants of the female parent selection.
3. Plants of the new *Alstroemeria* have red-colored flowers with pale yellow-colored centers whereas plants of the female parent selection have red-colored flowers with white-colored centers.

Plants of the new *Alstroemeria* can be compared to plants of the male parent selection. Plants of the new *Alstroemeria* differ from plants of the male parent selection in the following characteristics:

1. Plants of the new *Alstroemeria* are more compact than plants of the male parent selection.
2. Plants of the new *Alstroemeria* have smaller flowers than plants of the male parent selection.
3. Plants of the new *Alstroemeria* have red-colored flowers with pale yellow-colored centers whereas plants of the male parent selection have yellow-colored flowers with yellow-colored centers.

Plants of the new *Alstroemeria* can be compared to plants of the *Alstroemeria hybrida* 'Tesrobin', disclosed in U.S. Plant Pat. No. 19,345. In side-by-side comparisons, plants of the new *Alstroemeria* differ primarily from plants of 'Tesrobin' in the following characteristics:

1. Plants of the new *Alstroemeria* are taller than plants of 'Tesrobin'.
2. Plants of the new *Alstroemeria* have red-colored flowers with pale yellow-colored centers whereas plants of 'Tesrobin' have red-colored flowers with red and white-colored centers.

BRIEF DESCRIPTION OF THE PHOTOGRAPH

The accompanying colored photograph illustrates the overall appearance of the new *Alstroemeria* plant showing the colors as true as it is reasonably possible to obtain in colored reproductions of this type. Colors in the photograph may differ slightly from the color values cited in the detailed botanical description which accurately describe the colors of the new *Alstroemeria* plant.

The photograph (FIG. 1) comprises a side perspective view of typical flowering plants of 'Tessumred' grown in a container.

DETAILED BOTANICAL DESCRIPTION

Plants used for the aforementioned photograph and following observations and measurements were grown during the spring and summer in 24-cm containers in a glass-covered greenhouse in De Kwakel, The Netherlands. During the production of the plants, day temperatures ranged from 12° C. to 20° C. and night temperatures ranged from 10° C. to 16° C. Plants used in the photograph and description were three months old. Color references are made to The Royal Horticultural Society Colour Chart, 2015 Edition, except where general terms of ordinary dictionary significance are used.

Botanical classification: *Alstroemeria hybrida* 'Tessumred'.

Parentage:

*Female, or seed, parent.*—Proprietary selection of *Alstroemeria hybrida* identified as code number Zh4745a, not patented.

*Male, or pollen, parent.*—Proprietary selection of *Alstroemeria hybrida* identified as code number E1001, not patented.

Propagation:

*Type.*—By root divisions.

*Time to produce a rooted young plant, summer.*—About 30 days at temperatures about 20° C.

*Time to produce a rooted young plant, winter.*—About 40 days at temperatures about 16° C.

*Root description.*—Fibrous and fleshy; thin; typically white in color, actual color of the roots is dependent on substrate composition, water quality, fertilizer type and formulation, substrate temperature and physiological age of roots.

*Rooting habit.*—Freely branching; medium density.

*Rhizome length.*—About 19 cm.

*Rhizome diameter.*—About 6 mm.

*Rhizome texture.*—Somewhat rugose, glabrous.

*Rhizome color.*—Close to 162D.

Plant description:

*Plant and growth habit.*—Herbaceous perennial; broadly upright plant habit; overall shape, flattened globular to broadly oblong; freely basal branching habit with about 38 primary lateral branches developing per plant; sturdy and strong plants; vigorous growth habit; moderate growth rate.

*Plant height, soil level to top of foliar plane.*—About 36.5 cm.

*Plant height, soil level to top of floral plane.*—About 45.6 cm.

*Plant diameter* (*area of spread*).—About 56.1 cm.

Lateral branch description:

*Aspect.*—Mostly upright to about 70° from vertical; average is about 35° from vertical.

*Length.*—About 36.5 cm.

*Diameter.*—About 6 mm.

*Internode length.*—About 1.4 cm.

*Strength.*—Moderately strong.

*Texture and luster.*—Smooth, glabrous, waxy; matte.

*Color, developing.*—Close to 144C.

*Color, developed.*—Close to 144B slightly to strongly tinged with close to between N186C and 200B; waxy cuticle, distally close to 144D and proximally, close to N187D.

Leaf description:

*Arrangement.*—Alternate; below the peduncles in a single whorl; simple.

*Length.*—About 6.6 cm.

*Width.*—About 2.1 cm.

*Shape.*—Narrowly ovate to narrowly elliptic; twisting.

*Apex.*—Acute.

*Base.*—Cuneate.

*Margin.*—Entire.

*Texture and luster, upper surface.*—Smooth, glabrous; matte.

*Texture and luster, lower surface.*—Smooth, glabrous; slightly glossy.

*Venation pattern.*—Parallel.

*Color.*—Developing leaves, upper surface: Surface faces downwards; close to between 138A and 139C. Developing leaves, lower surface: Surface faces upwards; close to 143A. Fully expanded leaves, upper surface: Surface faces downwards; close to between 147B and 191A; venation, close to between 146B and 147B. Fully expanded leaves, lower surface: Surface faces upwards; close to 137A; venation, close to 137A.

*Petioles.*—Length: About 2.5 cm. Diameter: About 2 mm by 6 mm. Texture and luster, upper surface: Smooth, glabrous; matte. Texture and luster, lower surface: Smooth, glabrous; moderately glossy. Color, upper surface: Close to between 143B and 144A. Color, lower surface: Close to 143B.

Flower description:

*Flower type and habit.*—Single zygomorphic flowers arranged in terminal compound umbels; flowers face mostly outwardly to slightly upright; perianth segments separate; freely flowering habit with about ten flowers per inflorescence and about 130 flowers per plant.

*Natural flowering season.*—Plants begin flowering about eight weeks after planting; flowering continuous from late spring into the summer in The Netherlands.

*Fragrance.*—None detected.

*Flower longevity on the plant.*—About ten days; flowers not persistent.

*Flower buds.*—Length: About 3 cm. Diameter: About 1.1 cm. Shape: Obovate. Texture and luster: Smooth, glabrous; matte. Color: Close to 53B to 53C; towards the base, close to 145C to 145D; venation, close to 146A and 147A.

*Umbel height.*—About 11.8 cm.

*Umbel diameter.*—About 14.8 cm.

*Flower diameter* (*horizontal*).—About 5.9 cm.

*Flower length* (*vertical*).—About 6.1 cm.

*Flower depth* (*height*).—About 5.4 cm.

*Perianth.*—Arrangement: Six arranged in two whorls, each whorl with two lateral and one median segments. Size, inner perianth: Length, lateral segments: About 5.6 cm. Width, lateral segments: About 1.5 cm. Length, median segment: About 4.6 cm. Width, median segment: About 1.4 cm. Size, outer perianth: Length, lateral segments: About 5 cm. Width, lateral segments: About 2.3 cm. Length, median segment: About 5.1 cm. Width, median segment: About 2.4 cm. Shape, inner perianth, lateral and median segments: Oblanceolate. Shape, outer perianth, lateral and median segments: Obcordate. Apex, inner perianth, lateral and median segments: Abruptly acute. Apex, outer perianth, lateral and median segments: Emarginate. Base, inner perianth, lateral and median segments: Narrowly cuneate. Base, outer perianth, lateral and median segments: Long cuneate. Margin, inner and outer perianths, lateral and median segments: Entire. Texture and luster, inner and outer perianths, lateral and median segments, upper surface: Smooth, glabrous; velvety; matte. Texture and luster, inner and outer perianths, lateral and median segments, lower surface: Smooth, glabrous; slightly glossy. Color, inner perianth: When opening, lateral segments, upper surface: Towards the apex, close to between 47A and 53B; center, close to 6C; towards the base, close to 52C; spots and stripes, close to between N186C and 202A. When opening, median segment, upper surface: Close to 50A; towards the base, close to 48B; stripes, close to between N186C and 202A. When opening, lateral segments, lower surface: Towards the apex, close to between 53B and 59C; center, close to 5C; towards the base, close to 54B and 53B to 53C; spots and stripes, close to 201B. When opening, median segment, lower surface: Close to 51A; towards the base, close to 51D; stripes, close to 201B to 201C. Fully opened, lateral segments, upper surface: Towards the apex, close to 47B; center, close to 4D; towards the base, close to 55C to 55D; spots and stripes, close to between N186C and 202A; color does not change with development. Fully opened, median segment, upper surface: Close to 47B; towards the base, close to 48B; stripes, close to between 53A and N186C; color does not change with development. Fully opened, lateral segments, lower surface: Towards the apex, close to 58B; center, close to 4D to lighter than 4D; towards the base, close to 53C; spots and stripes, close to 201B; color does not change with development. Fully opened, median segment, lower surface: Close to 53D; towards the base, close to 54D; stripes, close to 201C to 201D; color does not change with development. Color, outer perianth: When opening, lateral and median segments, upper surface: Close to 53C; towards the margins, close to 47B; at the apex, close to 59B to 59C; towards the base, close to 54C. When opening, lateral and median segments, lower surface: Close to 53C to 53D; towards the base, close to 54B; at the apex, close to 147B; venation, close to 143A to 143C. Fully opened, lateral and median segments, upper surface: Close to 47A; towards the margins, close to 47C; at the apex, close to 53B; towards the base, close to 48B; color does not change with development. Fully opened, lateral and median segments, lower surface: Close to 53C; towards the base, close to 53D and 54B; at the apex, close to 147B; venation, close to 152C to 152D; color does not change with development.

*Pedicels.*—Length: About 2 cm. Diameter: About 2 mm. Strength: Moderately strong to strong. Angle: About 10° from stem axis. Texture and luster: Smooth, glabrous; slightly glossy. Color, upper and lower surfaces: Close to 146B.

*Reproductive organs.*—Stamens: Quantity per flower: Six. Filament length: About 4 cm. Filament color: Close to 47D; towards the base, close to 49C. Anther shape: Oblong. Anther size: About 9 mm by 3 mm. Anther color: Close to 42B. Pollen amount: Moderate. Pollen color: Close to 162A. Pistils: Quantity per flower: One. Pistil length: About 4 cm. Style length: About 3.6 cm. Style color: Close to 47B; towards the base, close to 49C. Stigma diameter: About 8 mm. Stigma shape: Tri-parted; parts, club-shaped, curved. Stigma color: Close to 158D. Ovary color: Close to 146B.

*Fruits and seeds.*—To date, fruit and seed development have not been observed on plants of the new *Alstroemeria*.

Pathogen & pest resistance: Plants of the new *Alstroemeria* have not been observed to be resistant to pathogens and pests common to *Alstroemeria* plants.

Garden performance: Plants of the new *Alstroemeria* have been observed to have good garden performance and to tolerate high temperatures of about 35° C. and to be suitable for USDA Hardiness Zones 7 to 10.

It is claimed:

1. A new and distinct *Alstroemeria* plant named 'Tessumred' as illustrated and described.

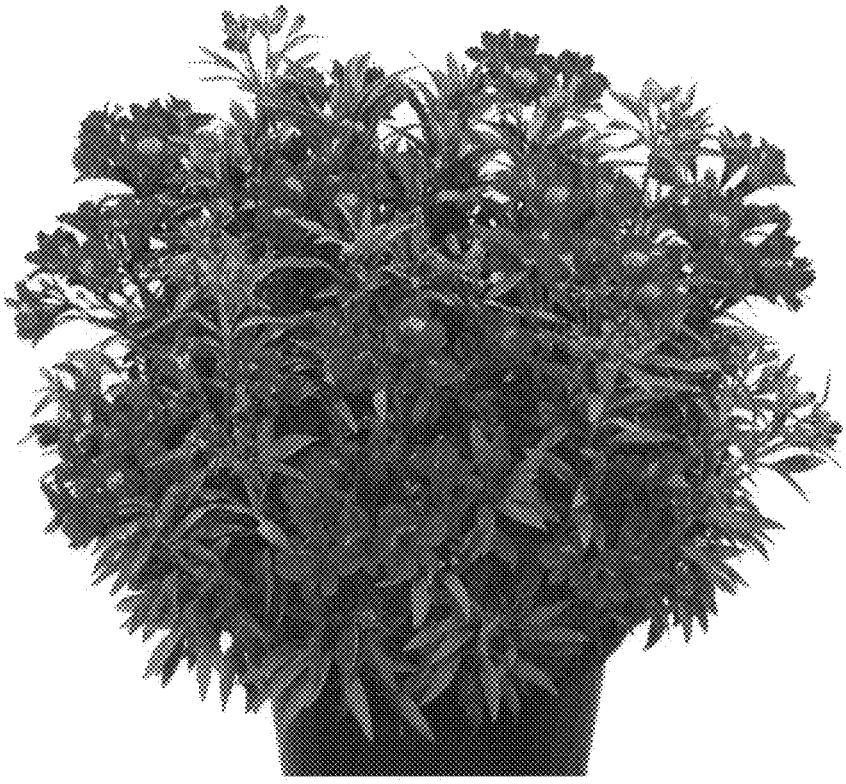

* * * * *